United States Patent [19]
Norton et al.

[11] 4,355,194
[45] Oct. 19, 1982

[54] METHOD FOR PREPARING HIGH DENSITY LIQUID HYDROCARBON FUELS

[75] Inventors: Richard V. Norton, Dublin; Dennis H. Fisher, Westerville; Garry M. Graham, Plain City; Peter J. Frank, Westerville, all of Ohio

[73] Assignee: Ashland Oil, Inc., Ashland, Ky.

[21] Appl. No.: 204,436

[22] Filed: Nov. 6, 1980

[51] Int. Cl.³ ............................................. C01L 1/04
[52] U.S. Cl. .................................... 585/14; 60/208; 149/109.4; 585/22; 585/23; 585/362
[58] Field of Search ............... 60/208, 211; 149/109.4; 585/14, 22, 23, 274, 362

[56] References Cited

U.S. PATENT DOCUMENTS

| | | | |
|---|---|---|---|
| 4,222,800 | 9/1980 | Myers, Jr. et al. | 60/208 X |
| 4,225,735 | 9/1980 | Hall, Jr. et al. | 60/208 X |
| 4,275,254 | 6/1981 | Schneider et al. | 60/211 X |
| 4,278,823 | 7/1981 | Schneider et al. | 60/208 X |
| 4,286,109 | 8/1981 | Norton et al. | 585/22 X |

OTHER PUBLICATIONS

The Condensed Chemical Dictionary, 9th Ed., 1977, Van Nostrand Reinhold Co., New York, p. 590.

*Primary Examiner*—Leland A. Sebastian
*Attorney, Agent, or Firm*—William Kammerer

[57] ABSTRACT

A method for catalytically isomerizing a mixture of hexacyclic dimers obtained by dimerizing norbornadiene in the presence of a zero valent iron complex whereby the hydrogenated derivatives of the resultant isomerization product exhibits substantially lower freeze point than that associated with the hydrogenated derivatives of said precursor dimer mixture, the latter representing the highest energy liquid hydrocarbon fuel commercially available.

4 Claims, No Drawings

METHOD FOR PREPARING HIGH DENSITY LIQUID HYDROCARBON FUELS

BACKGROUND OF THE INVENTION

1. Field of the Invention

This invention relates to a method for synthesizing high density liquid hydrocarbon fuels.

2. Description of the Prior Art

High density liquid hydrocarbon fuels are characterized in having a net volumetric heat of combustion in excess of about 140,000 BTU per gallon. A high density or energy fuel is essentially required for fueling turbojet and ramjet propelled limited volume missile systems. Beyond the need for a high energy content in order to achieve an adequate range performance of the missile, there are other requirements in the forefront depending in the main on the manner in which the missile is to be deployed. For instance, the operational conditions encountered in the deployment of certain missile systems call for the use of a fuel having the highest energy content consistent with having a freeze point substantially below 0° F. and being reasonably fluid at a temperature near its freeze point.

A high density fuel of the foregoing type does not occur in nature but rather must be chemically synthesized. Essentially all of the current generation of such fuels commonly feature a norbornane moeity having an additional cyclic hydrocarbon appendage. A particularly noteworthy fuel of the foregoing type is represented by the exo stereo isomer of tetrahydrodicyclopentadiene which in commerce is referred to as JP-10 fuel. The latter is prepared by first hydrogenating dicyclopentadiene yielding the solid endo-isomer of the hydrogenated derivative. The endo structure is then isomerized in the presence of a catalyst to produce the exo-isomer almost quantitatively in a relatively pure form. Since JP-10 is derived from an abundantly available raw material coupled with the fact that the indicated isomerization procedure is highly effective and relatively facile, such are the main factors why the product is regarded to be an important high energy fuel.

Since JP-10 has a heat value of about 140,000 BTU per gallon it is not used by itself to fuel the more advanced second generation turbojet missile systems where maximum range performance is of primary consideration. In order to obtain a composite fuel of a suitable heat value for the indicated purpose, JP-10 is blended with the highest energy fuel currently available; viz., RJ-5, a structurally related fuel having a heat value of 161,000 BTU per gallon. This fuel is chemically described as the hydrogenated dimers of norbornadiene. The process for producing RJ-5 initially involves dimerizing norbornadiene in the presence of a zero valent iron complex. The dimerization step in accordance with the prior art results in the formation of three principle stereo isomer species with the major species being the endo, endo isomer, generally referred to simply as the unsaturated HNN isomer. Due to its substantial HNN content, RJ-5 exhibits such a high freezing temperature that it can be blended with JP-10 only to a limited extent before creating fuel delivery problems of significant magnitude in the missile systems referred to above.

Accordingly the object of this invention is that of beneficially modifying the isomeric makeup of the unsaturated dimer precursors of RJ-5, specifically the HNN content thereof, which upon hydrogenation provides a liquid eutectic mixture capable of blending with a minor proportion of JP-10 to produce a fuel of improved low temperature performance capability.

SUMMARY OF THE INVENTION

In accordance with the present invention a method is provided for altering the isomeric distribution of a mixture of hexacylic dimers prepared by dimerizing norbornadiene in the presence of a zero valent iron complex. The method comprises isomerizing the hexacylic dimer mixture in the presence of an alumina silica catalyst whereby the normally predominant endo, endo isomer component is reduced to about 10-35 weight percent of the overall isomeric mixture. The contemplated isomerization procedure results in essentially a doubling of the readily identifiable isomer species present in the starting dimer mixture. Hydrogenation of the resultant isomerized product provides a eutectic mixture of isomers exhibiting a substantially lower freeze point as compared to the hydrogenated derivatives of the precursor isomers.

DESCRIPTION OF THE PREFERRED EMBODIMENTS

As indicated hereinabove RJ-5 is a commercially available high density fuel. Complete details relative to the preparation thereof can be found set forth in U.S. Pat. Nos. 3,282,663, 3,326,992 and 3,377,398. The preferred procedure as the first step involves dimerizing norbornadiene in the presence of a catalyst system consisting of zero valent iron complexed with norbornadiene monomer and/or dimer ligands. The catalyst is prepared by reacting an organic iron complex with the iron present as $Fe^{+3}$ or $Fe^{+2}$ and a reducing agent. The preferred complex is one wherein the organic liquid is acetylacetonate and iron is present as $Fe^{+3}$. The preferred reducing agent is a trialkyl aluminum and specifically aluminum triethyl. A further delineation of the process parameters involved in effecting dimerization can be found in the cited patents.

In dimerizing norbornadiene in accordance with this prior art, three principle isomers of the dimerized product are obtained. These comprise about 60-65% of HNN, 10% of PxTx (pentacyclic exo-trans-exo), and in the neighborhood of 20% of the HXN isomer. The resultant dimer mixture is hydrogenated in the presence of a hydrogenation catalyst, a variety of which exists for this purpose. The preferred catalyst, however, is nickel introduced in the form of nickel octoate and reduced by a trialkyl aluminum, and specifically triethyl aluminum. The hydrogenation product is distilled to provide a specification cut and then decolorized.

In the practice of the present invention the norbornadiene dimer mixture is isomerized prior to effecting the hydrogenation thereof in producing the contemplated high energy fuel. Isomerization is carried out by contacting the unsaturated hexacyclic dimers with an alumina silica catalyst at an elevated temperature. Suitable catalysts range in net silica content from about 10-90% and correspondingly in net alumina content from 90-100%. Only the alloyed compositions are effective inasmuch as silica and alumina per se do not evidence any significant catalytic activity in the present context. Representative of commercially available catalysts spanning the broad range of alumina and silica contents noted above include Davison #135 (87% $SiO_2$/13% $Al_2O_3$) and Porocel activated bauxite (6-9% $SiO_2$/

73–78% Al$_2$O$_3$). The catalyst compositions containing a high silica content; i.e., ≧80%, are preferred primarily because their use results in minimizing the formation of tetramers and polymers.

The amount of catalyst suitable for effecting isomerization is from about 1–10% based on the weight of the dimer mixture. The preferred amount of catalyst is from 2–4% on said basis. While any temperature ranging from about 170° C. up to the boiling point of the dimer mixture can be observed, the time required for effecting the contemplated degree of isomerization at the lower temperatures indicated requires a period of extended heating. Accordingly, the isomerization procedure particularly preferred consists of slurrying the catalyst with the dimer mixture, rapidly heating to the boiling point of the mixture (250°–260° C.) and holding for 3–20 minutes, and thereupon quenching upon attaining the desired reduction of the HNN isomer content. Depending on the amount of catalyst utilized, the holding time at the boiling temperature will be in the range of 5 to 10 minutes in order to achieve a reduction of the HNN content to 30% or less.

As indicated previously the hexacyclic dimer mixture prepared in accordance with the preferred procedure of the prior art results in a mixture of three principle isomers of which the HNN isomer predominates. In the practice of the present invention the HNN isomer is mainly rearranged whereas the other isomers are only minorly to insignificantly affected. According to gas chromatographic analysis, the HNN content is variously converted to three or four new isomers none of which have been structurally characterized. Of these new isomers two show up as major peaks on the analysis graph. The overall best results are realized by reducing the initial HNN content to between 25–30%. Although not preferred, it is within the spirit of this invention to reduce the HNN content to as low as 10% and blend back with the unisomerized dimer mixture in order to increase the overall HNN content to the preferred range. The hydrogenated derivatives of such blends likewise exhibit a substantially lower melting point. Alternatively, an isomerized product of low HNN content, i.e., less than 20%, can be hydrogenated and then blended with RJ-5 to provide the type of fuel composition contemplated.

EXAMPLE

Five batches of distilled norbornadiene dimer each averaging about 930 pounds were isomerized using two (2) weight percent Davison 135 silica-alumina catalyst per batch. Isomerization was conducted at atmospheric pressure in a 200 gallon stainless steel reactor. The respective reaction temperatures were in the order of from 485° F. to 515° F. The isomerization reaction for the individual batches at the applicable temperature was carried out for 5–12 minutes with the average time being about 10 minutes. A composite sample of the BCH dimer feed contained 60.6 weight percent of the HNN isomer as determined by gas chromatographic analysis. After isomerization, a composite of the product contained 28.9 weight percent HNN dimer. The isomerized dimer was hydrogenated, distilled and decolored following standard RJ-5 production practices. The resultant product was blended with JP-10 to provide a fuel blend containing 41.7 weight percent of the JP-10. The HNN isomer content of the blended fuel was 19.4 weight percent as determined by capillary gas chromatographic analysis.

The composite fuel of the example meets the key operational criteria established for a fuel designated RJ-6 for the Air Force ASALM missile program. These criteria are a maximum of 400 cs viscosity at −65° F., a freezing point lower than −65° F., and a heat value of at least 150,000 BTU/gallon.

What is claimed is:
1. In a method for preparing an isomeric mixture of the hexacylic dimer of norbornadiene containing a major amount of the endo, endo stereo isomer thereof wherein said diene is dimerized in the presence of a catalytic amount of a zero valent iron complex; the improvement of isomerizing said dimer mixture in the presence of an alumina silica catalyst to effect the reduction of the endo, endo isomeric content thereof to between about 10 and 35 weight percent.
2. The improvement in accordance with claim 1 wherein the endo, endo isomeric content of said dimer mixture is reduced to between about 25 and 30 weight percent.
3. A high density fuel composition comprising the substantially completely hydrogenated derivatives of the isomerized dimer mixture prepared in accordance with the improvement of claim 2.
4. A high density fuel composition consisting essentially of a blend of 35 to 45 parts by weight of exo-tetrahydrodicyclopentadiene and correspondingly from 65 to 55 parts of the fuel composition of claim 3.

* * * * *